United States Patent [19]

Blackwell, III

[11] 4,327,033

[45] Apr. 27, 1982

[54] PROCESS FOR THE PRODUCTION OF METHOMYL OXIME

[75] Inventor: Joseph T. Blackwell, III, Greensboro, N.C.

[73] Assignee: Ciba-Geigy Corporation, Ardsley, N.Y.

[21] Appl. No.: 205,811

[22] Filed: Nov. 10, 1980

[51] Int. Cl.³ .................................... C07C 119/16
[52] U.S. Cl. ........................................ 260/453.3
[58] Field of Search .............................. 260/453.3

[56] References Cited

U.S. PATENT DOCUMENTS 3,658,869  4/1972  Soloway et al. ............... 260/453.3
3,752,841  8/1973  Fuchs .
3,987,096  10/1976  Fuchs .

FOREIGN PATENT DOCUMENTS 1618913  1/1971  Fed. Rep. of Germany ... 260/453.3
676406  5/1963  South Africa ................... 260/453.3
1105879  6/1966  United Kingdom ............ 260/453.3

Primary Examiner—John M. Ford
Assistant Examiner—Robert C. Whittenbaugh
Attorney, Agent, or Firm—Karl F. Jorda

[57] ABSTRACT

A process is provided for the manufacture of methomyl oxime comprising the steps of chlorinating acetaldoxime dissolved in N-methylpyrrolidone at a temperature range of −10° C. to 0° C. to form a N-methylpyrrolidone solution of acethydroxamoyl chloride; thioesterifying the acethydroxyamoyl chloride in said solution at a temperature range of about 0° C. to 10° C. at pH in the range 6–7.

4 Claims, No Drawings

PROCESS FOR THE PRODUCTION OF METHOMYL OXIME

FIELD OF THE INVENTION

This invention relates to the synthesis of methomyl oxime also known as methyl thiolhydroxamate or methyl thiolacethydroxamate. More particularly, the invention relates to such synthesis through several stages in a specific solvent for these stages that promotes efficient reaction pathways at excellent yields in high purity.

BACKGROUND OF THE INVENTION

Methomyl oxime, m.p. 94°-97° C., is a commercial product (Aldrich 18,986-3 and is useful in the production of certain useful insecticides as the carbamate, Methomyl, and similar derivatives.

There are numerous references in the literature to the preparation of this economically useful intermediate and related alkyl thiolhydroxamates. Most of these prior art references are characterized by either low yields or high reaction dilutions. The yields have been low due to highly reactive nature of the reaction environment. To overcome this critical environmental factor, many of the prior art syntheses have been carried out at great dilution, thus the nature of the solvent and the degree of dilution are critical.

U.S. Pat. No. 3,987,096 discloses an aqueous process which gives yields of about 90% of methomyl oxime but at a reaction concentration of less than 1%. Such a low concentration hinders a viable production rate and is particularly wasteful of energy in the steps required for economic recovery of the valuable intermediate or its ultimate products.

Recently yields of similar magnitude of methomyl oxime have been reported in U.S. Pat. No. 3,752,841 where dimethylformamide (DMF) is used as the reaction solvent. This solvent permits reaction concentrations of about 20-25% and thus provides greater reaction efficiency. However DMF is a recognized irritant and toxicant substance requiring stringent precautions in the workplace under current safety legislation

SUMMARY OF THE INVENTION

This invention is based on the discovery that methomyl oxime can be prepared in good yields at high concentrations in a unique solvent lactam, N-methylpyrrolidone (NMP). The solvent, when used as the reaction medium in the two-stage synthesis from (1) acetaldoxime via chlorination to acethydroxamoyl chloride and then (2) thioesterification with methyl mercaptan to methomyl oxime, provides a catalytic or stabilizing effect on the first-stage reaction ensuring good yield of the desired product. The thus stabilized acethydroxamoyl chloride is completely and quantitatively thioesterified in the second-stage reaction in the NMP medium. Additionally this medium stabilizes the further conversion of the methomyl oxime via methyl isocyanate to Methomyl, the insecticide (Merck Index 9th Edition #5854).

DETAILED DESCRIPTION OF THE INVENTION

Acetaldoxime, the starting material, is prepared by reacting acetaldehyde with hydroxylamine sulfate in aqueous alkaline solution according to Equation (1).

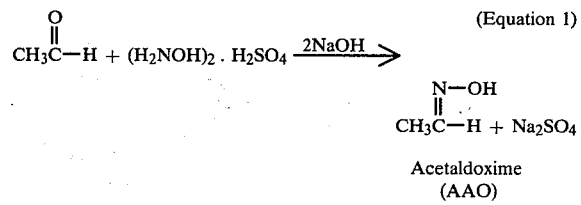

(Equation 1)

Acetaldoxime (AAO)

This reaction is well-documented in the literature. Using water as the solvent, 95% yields of AAO are obtained. Due to the high solubility of acetaldoxime in water, methylene chloride is used to extract it from the reaction mixture. The partition coefficient with methylene chloride is such that multiple extractions are required to remove most of the acetaldoxime from the reaction mixture.

The conversion of the acetaldoxime to methomyl oxime is in two stages. Stage (1) is the chlorination of the acetaldoxime to form acethydroxamoyl chloride (AHC) (Equation 2);

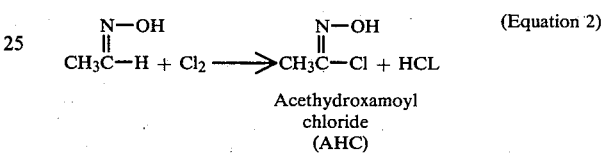

(Equation 2)

Acethydroxamoyl chloride (AHC)

This reaction is preferably carried out at about 15-25% concentration of AAO in order to provide sufficient solvent capability after precipitation of NMP.HCl. As the acethydroxamoyl chloride is very labile it is not convenient to isolate it from its reaction mixture as after removal of the solvent the residue became spontaneously hot indicating unwanted side reactions.

Because of this difficulty of isolation of the acethydroxamoyl chloride, the thioesterification with methyl mercaptan according to Equation 3 is carried out in situ (Stage 2).

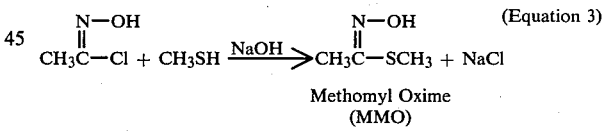

(Equation 3)

Methomyl Oxime (MMO)

Since an authentic standard of acethydroxamoyl chloride could not be obtained, the reactions were followed by high pressure liquid chromotography (HPLC). From HPLC it was clear that the chlorination reaction (Equation 2) when conducted in $H_2O$ or $CH_2Cl_2$ produced highly complex reaction mixtures but when conducted in N-methylpyrrolidone, HPLC indicated the production of predominantly one component. In addition, after the addition of the methyl mercaptan and caustic, HPLC indicated that the thioesterification was straight-forward and therefore the chlorination (Equation 2) is the yield limiting step.

The presence of water in the NMP reaction medium has also been found to reduce the ultimate yield of methomyl oxime. Water interferes with the catalytic and stabilizing effects of N-methylpyrrolidone in the chlorination reaction. The presence of an amount of water in the medium in excess of about 10% reduces the yield. A 25% water content reduces the yield by about one third.

In fact, the yield with such a mixture is almost the same as with water alone.

The reaction of Equation 2 is carried out at temperatures of 0° C. to −10° C. During the chlorination, the rate of chlorine introduction is adjusted to keep the mixture at −10° C. to 0° C.

When the addition of chlorine is completed, the mixture is preferably maintained below 0° C. for at least 10, preferably 15, and up to about 30 minutes to assure completion of the chlorination.

The methyl mercaptan is added to the stirred slurry of acethydroxamoyl chloride dissolved in N-methylpyrrolidone which is suspended any precipitated NMP.HCl. (This, of course, can be removed before the addition of the mercaptan.)

The mercaptan is added to the cold mixture and then the mixture is diluted and caustic (50% NaOH solution) is added to neutralize the reaction mixture to pH 6–7. The amount of caustic needed, of course, will vary depending on whether or not the N-methylpyrrolidone hydrochloride has been removed. This step should be conducted at temperatures of 0° C. to +10° C. and a slight excess of $CH_3SH$ (about 5%) is used during the thioesterification.

MMO in aqueous media at 25° C. was stable after 72 hours at pH 7–12 but at pH 2 was 12% decomposed in 24 hours and 18% decomposed in 72 hours. Solid MMO showed no decomposition after 24 hours at 74° but was 93% decomposed after 48 hours at 105° C. TGA showed a rapid loss of weight beginning at about 75° C. DSC showed an endotherm beginning at about 80° C. followed by an exotherm at about 155° C.; the DSC is then stable up to 260° C.

The following Examples illustrate the presently preffered mode of the invention. Parts and percentages are by weight unless otherwise specified.

EXAMPLE 1

A one-liter, 5-necked flask was equipped with a mechanical stirrer, pH probe, sparge tube, addition funnel, thermometer and condenser. A 59 gm (1 mole) acetaldoxime and 236 g N-methylpyrrolidone was charged to the flask. This solution was cooled to about −5° C., and 71 g (1 mole) chlorine gas was sparged into the reaction mixture at such a rate that the temperature did not exceed 0° C. When the $Cl_2$ addition was completed, the reaction was held at 0° C. for about 15 minutes. Then 50.4 g (1.05 mole) methyl mercaptan was added, followed by 150 g $H_2O$. To this was added dropwise about 160 g of a solution of 50% caustic until the pH reached 6–7. During this addition the temperature did not exceed 5° C. When the pH 6–7 was reached, the reaction was held at 0° C. to 5° C. for 30 minutes. The NaCl cake was filtered off. The yield in solution of methomyl oxime was 80–90%.

EXAMPLE 2

A 256 g portion of an N-methyl pyrrolidone solution of methomyl oxime (containing 0.4 mole MMO) and 0.5 g triethylamine was charged to a 500 ml 5-necked flask. To this was added 28.7 g (0.5 mole) methyl isocyanate rapidly. The temperature rose to 40° C. for 1.0 hour. The reaction mixture was then transferred to a Kugelrohr apparatus, and the solvent removed at reduced pressure. A yield of 96% Methomyl, assaying >99% was realized.

EXAMPLE 3

The process according to this invention can also be used in the processes of preparing intermediates of the formula:

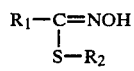

where $R_1$ is lower alkyl ($C_1$–$C_3$) or lower methoxyalkyl and $R_2$ is lower alkyl ($C_1$–$C_3$) or cyanoalkyl. The N-methylpyrrolidone promotes these reactions.

The procedure according to Example 1 was repeated but using the indicated aldoximes and mercaptans. Similar yields under equivalent conditions were obtained.

| Example | Aldoxime | Mercaptan |
| --- | --- | --- |
| 4 | acetaldoxime | ethylmercaptan |
| 5 | propionaldoxime | methylmercaptan |
| 6 | propionaldoxime | ethylmercaptan |
| 7 | propionaldoxime | propylmercaptan |
| 8 | methoxyacetaldoxime | methylmercaptan |
| 9 | methoxyacetaldoxime | ethylmercaptan |
| 10 | methoxyacetaldoxime | propylmercaptan |
| 11 | acetaldoxime | cyanoethylmercaptan |

The invention that is claimed is:

1. In the process for the manufacture of alkylthio hydroxamates of the formula:

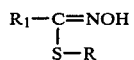

where $R_1$ is lower alkyl or lower methoxyalkl; and $R_2$ is lower alkyl or lower cyanoalkyl by chlorinating an aldoxime of the formula:

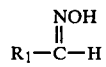

at a temperature range of −10° C. to 0° C. to form an alkylhydroxamic acid chloride of the formula

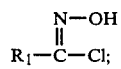

and then thioesterifying said alkylhydroxamic acid chloride at a temperature range of about 0° C. to 10° C. at a pH in the range 6–7, the improvement which comprises employing N-methylpyrrolidone as solvent in both reaction steps.

2. A process according to claim 1 for the manufacture of methomyl oxime which comprises the steps of chlorinating acetaldoxime dissolved in N-methylpyrrolidone at a temperature range of −10° C. to 0° C. to form a N-methylpyrrolidone solution of acethydroxamoyl chloride; thioesterifying the acethydroxyamoyl chloride in said solution at a temperature range of about 0° C. to 10° C. at pH in the range 6–7.

3. The process according to claim 2 wherein chlorine gas is the chlorination agent in said chlorination step.

4. The process according to claim 2 wherein methyl mercaptan is the thioesterification agent in said thioesterification step.

* * * * *